US010254269B2

(12) United States Patent
Miller et al.

(10) Patent No.: US 10,254,269 B2
(45) Date of Patent: Apr. 9, 2019

(54) SAMPLING AN OIL COMPOSITION FOR ENHANCING RECOVERY OF OIL COMPONENTS

(71) Applicant: Energy & Environmental Research Center Foundation, Grand Forks, ND (US)

(72) Inventors: David J. Miller, Grand Forks, ND (US); Steven B. Hawthorne, Grand Forks, ND (US)

(73) Assignee: Energy & Environmental Research Center Foundation, Grand Forks, ND (US)

( * ) Notice: Subject to any disclaimer, the term of this patent is extended or adjusted under 35 U.S.C. 154(b) by 186 days.

(21) Appl. No.: 14/825,361

(22) Filed: Aug. 13, 2015

(65) Prior Publication Data
US 2016/0047791 A1 Feb. 18, 2016

Related U.S. Application Data

(60) Provisional application No. 62/037,732, filed on Aug. 15, 2014.

(51) Int. Cl.
*G01N 33/28* (2006.01)
(52) U.S. Cl.
CPC ............... *G01N 33/2841* (2013.01)
(58) Field of Classification Search
CPC ............ G01N 33/2841; G01N 33/24
USPC ........................................ 73/53.05
See application file for complete search history.

(56) References Cited

U.S. PATENT DOCUMENTS

| 4,455,860 | A | * | 6/1984 | Cullick | G01N 33/2823 73/19.11 |
|---|---|---|---|---|---|
| 4,589,486 | A | * | 5/1986 | Brown | E21B 43/164 166/252.1 |
| 4,766,558 | A | * | 8/1988 | Luks | E21B 43/16 166/252.1 |
| 8,881,577 | B1 | * | 11/2014 | Agar | E21B 49/005 73/54.06 |
| 9,851,339 | B2 | | 12/2017 | Hawthorne et al. | |
| 9,879,522 | B2 | | 1/2018 | Hawthorne | |
| 2006/0289157 | A1 | | 12/2006 | Rao | |
| 2008/0173076 | A1 | * | 7/2008 | Robin | G01N 33/28 73/61.78 |
| 2011/0088895 | A1 | * | 4/2011 | Pop | E21B 7/04 166/254.2 |
| 2014/0232853 | A1 | | 8/2014 | Lewis | |
| 2014/0338753 | A1 | | 11/2014 | Sperling et al. | |
| 2015/0059446 | A1 | | 3/2015 | Agar et al. | |
| 2015/0060057 | A1 | | 3/2015 | Hawthorne et al. | |
| 2015/0238966 | A1 | * | 8/2015 | Berndt | B01L 3/0262 436/179 |
| 2015/0283541 | A1 | | 10/2015 | Curran et al. | |
| 2015/0330962 | A1 | * | 11/2015 | Aquino Olivos | G01N 33/28 436/141 |
| 2016/0047226 | A1 | | 2/2016 | Hawthorne et al. | |

FOREIGN PATENT DOCUMENTS

| GB | 2443077 B | 3/2011 | |
|---|---|---|---|
| WO | WO 2014037506 A1 * | 3/2014 | ............ B01L 3/0262 |
| WO | WO-2015/031341 A1 | 3/2015 | |

OTHER PUBLICATIONS

"U.S. Appl. No. 14/470,241, Non Final Office Action dated Nov. 28, 2016", 26 pgs.
"U.S. Appl. No. 14/470,241, Response filed Feb. 22, 2017 to Non Final Office Action dated Nov. 28, 2016", 12 pgs.
"U.S. Appl. No. 14/825,351, Non Final Office Action dated Nov. 18, 2016", 4 pgs.
"U.S. Appl. No. 14/825,351, Response filed Feb. 21, 2017 to Non Final Office Action dated Nov. 18, 2016", 8 pgs.
"Chinese Application Serial No. 201480047982.8, Office Action dated Aug. 18, 2016", W/English Translation, 24 pgs.
"Chinese Application Serial No. 201480047982.8, Response filed Jan. 3, 2017 to Office Action dated Aug. 18, 2016", w/ English Claims, 11 pgs.
"Determination of Minimum Miscibility Pressure of Formation Oil and Carbon Dioxide in Daluhu Oilfield Fan Block 124", w/ English Abstract—Oil Gas Geology and Recovery Rate, vol. 9, No. 6, (Dec. 31, 2002), 4 pgs.
"European Application Serial No. 14771415.8, Response filed Nov. 18, 2016 to Communication pursuant to Rules 161(2) and 162 EPC dated May 9, 2016", 12 pgs.
Ping, Guo, et al., "Determination of Minimum Miscibility Pressure of Carbon Dioxide in Dagang Oilfield", w/ English Abstract Southwest College Journal, vol. 21, No. 3—19-21, (Aug. 31, 1999), 5 pgs.
"International Application Serial No. PCT/US2014/052674, International Preliminary Report on Patentability dated Mar. 10, 2016", 8 pgs.
"International Application Serial No. PCT/US2014/052674, International Search Report dated Oct. 28, 2014", 3 pgs.
"International Application Serial No. PCT/US2014/052674, Written Opinion dated Oct. 28, 2014", 6 pgs.
Ayirala, Subhash C, "Measurement and Modeling of Fluid-Fluid Miscibility in Multicomponent Hydrocarbon Systems", A Dissertation Submitted to the Graduate Faculty of the Louisiana State University and Agricultural and Mechanical College in partial fulfillment of the Requirements for the degree of Doctor of Philosophy in The Department of Petroleum Engineering, (Aug. 2005), 205 pgs.

(Continued)

*Primary Examiner* — Natalie Huls
*Assistant Examiner* — Monica S Young
(74) *Attorney, Agent, or Firm* — Schwegman Lundberg & Woessner, P.A.

(57) ABSTRACT

Various embodiments disclosed relate to methods and apparatus for sampling an oil composition. In various embodiments, the present invention provides a method of sampling one or more components of an oil composition. The method includes placing a fluid into a pressure chamber at a first pressure. The pressure chamber includes an oil composition therein. The oil composition contacts the fluid. The fluid includes at least one of a gas, a liquid, and a supercritical fluid. The method also includes taking a sample of at least one of the fluid and the oil composition from the pressure chamber.

19 Claims, No Drawings

(56) References Cited

OTHER PUBLICATIONS

Rao, Dandina N., "A new technique of vanishing interfacial tension for miscibility determination", *Fluid Phase Equilibria*, 139(1-2), (1997), 311-324.
"U.S. Appl. No. 14/470,241, Final Office Action dated May 1, 2017", 27 pgs.
"U.S. Appl. No. 14/470,241, Response filed Jun. 30, 2017 to Final Office Action dated May 1, 2017", 15 pgs.
"U.S. Appl. No. 14/825,351, Ex Parte Quayle Action mailed Apr. 25, 2017", 6 pgs.
"U.S. Appl. No. 14/825,361, Response filed Jun. 22, 2017 to Ex Parte Quayle Action mailed Apr. 25, 2017", 8 pgs.
"Chinese Application Serial No. 201480047982.8, Office Action dated May 11, 2017", 14 pgs.
Petitjeans, P, et al., "Miscible displacements in capillary tubes", J. Fluid Mech vol. 326, (May 6, 1996), 37-56.
"Chinese Application Serial No. 201480047982.8, Office Action dated Nov. 16, 2017", W/English Translation, 10 pgs.
"Chinese Application Serial No. 201480047982.8, Response filed Feb. 1, 2018 to Office Action dated Nov. 16, 2017", W/English Claims, 10 pgs.

\* cited by examiner

SAMPLING AN OIL COMPOSITION FOR ENHANCING RECOVERY OF OIL COMPONENTS

CROSS-REFERENCE TO RELATED APPLICATION

This application claims the benefit of priority to U.S. Provisional Patent Application Ser. No. 62/037,732, filed Aug. 15, 2014, the disclosure of which is incorporated herein in its entirety by reference.

BACKGROUND

Crude oil miscibility pressure with different fluids is an important parameter to optimize for enhanced oil recovery. The "minimum miscibility pressure," or "MMP," is an operating parameter that is useful for the successful operation of enhanced oil recovery processes such as the injection of fluids including, but not limited to, carbon dioxide, natural gas, and nitrogen into an oil reservoir. The injection of such fluids can increase production from the treated subterranean formation by at least one of swelling the crude oil, reducing oil viscosity, and forming a mobile phase including the injected fluid and oil components.

At various pressures and temperatures, such as the pressures and temperatures similar to those experienced downhole, the composition of an oil composition and the composition of a fluid in contact with the oil composition is difficult to determine.

SUMMARY OF THE INVENTION

Various embodiments of the present invention provide a method of sampling one or more components of an oil composition. The method includes placing a fluid into a pressure chamber at a first pressure. The pressure chamber includes an oil composition therein that contacts the fluid. The fluid includes at least one of a gas, a liquid, and a supercritical fluid. The method can include taking a sample of at least one of the fluid and the oil composition from the pressure chamber. In some embodiments, the method includes characterizing at least one aspect of the sample.

Various embodiments of the present invention provide an apparatus for sampling at least one component of an oil composition. The apparatus includes a pressure chamber configured to have oil composition therein The pressure chamber is configured to have a fluid including at least one of a gas, a liquid, and a supercritical fluid placed therein at a first pressure sufficient to contact the oil composition. The pressure chamber is configured such that a sample of at least one of the fluid and the oil composition can be taken at the first pressure.

DETAILED DESCRIPTION OF THE INVENTION

Reference will now be made in detail to certain embodiments of the disclosed subject matter. While the disclosed subject matter will be described in conjunction with the enumerated claims, it will be understood that the exemplified subject matter is not intended to limit the claims to the disclosed subject matter.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

The term "downhole" as used herein refers to under the surface of the earth, such as a location within or fluidly connected to a wellbore.

The term "fluid" as used herein can refer to a liquid, a gas, a supercritical fluid, or any suitable combination thereof.

Crude oil miscibility pressure with different fluids is an important parameter to optimize enhanced oil recovery. Two fluids can be defined as miscible at temperature conditions and pressure conditions where the interfacial tension between the fluids is zero. However, generally, crude oil is found as a mixture of a wide variety of hydrocarbons, each having a different molecular weight. If each of the components of crude oil were purified and individually tested for MMP with a fluid, a variety of different MMPs would be found, with generally lower MMPs for lower molecular weight materials and generally higher MMPs for higher molecular weight materials. As the pressure of a fluid with an oil composition that includes a mixture of materials is increased, a portion of the oil composition that can be predominantly the lowest molecular weight portions of the oil composition can become miscible with or substantially soluble in the fluid first (e.g., those components of the oil composition having an MMP, if MMP was measured for the purified components, that is at or lower than the pressure of the fluid), while another portion oil the oil composition that can be predominantly the higher molecular weight components can remain immiscible with or insoluble with the fluid (e.g., those components of the oil composition having an MMP, if MMP was measured for the purified component, that is higher than the pressure of the fluid). As the pressure is increased, a greater proportion of the oil composition becomes miscible with or substantially soluble in the fluid, such as the higher molecular weight species in the oil composition. In various embodiments, for oil compositions including a mixture of species having a range of at least one of molecular weights, structures, and properties, and a corresponding range of pressures over which various proportions of the oil composition are miscible with a given fluid due to different individual MMPs for various component of the oil composition (if measured in a purified state), the MMP can be defined as the minimum pressure wherein about 50 wt % of the oil composition is miscible with (e.g., experiences zero interfacial tension with) or is solubilized in the fluid (e.g., is substantially in the fluid phase and is substantially not in the oil composition phase), or wherein about 40 wt % to about 60 wt %, about 30 wt % to about 70 wt %, or about 1 wt % or less, or about 2 wt %, 3, 4, 5, 6, 7, 8, 9, 10, 12, 14, 15, 20, 25, 30, 35, 40, 45, 50, 55, 60, 65, 70, 75, 80, 85, 90, 95, 96, 97, 98, or about 99 wt % or more of the oil composition becomes miscible with or is solubilized in the fluid.

Various embodiments of the present invention provide a method of sampling one or more components of an oil composition. The method includes placing a fluid into a pressure chamber at a first pressure. The fluid includes at least one of a gas, a liquid, and a supercritical fluid. The fluid can be any suitable fluid described herein. The pressure chamber can be any suitable pressure chamber as described herein; however, the pressure chamber need not include capillary tubes. In some embodiments, the pressure chamber includes the capillary tubes, while in other embodiments the pressure chamber is free of capillary tubes. The pressure chamber can include a viewing window, or the pressure chamber can be free of a viewing window. The pressure chamber includes an oil composition therein that contacts the fluid. The oil composition is any suitable oil composition as described herein, such as an oil composition having multiple components, wherein one or more of the multiple components have different MMPs with the fluid if measured with the component in a substantially purified state. The method can include taking a sample of at least one of the fluid and the oil composition from the pressure chamber. The sample of the fluid can include any portions of the oil composition that are miscible with or substantially soluble in the fluid at the first pressure and at the temperature conditions used. The sample of the oil composition can include any portions of the oil composition that are immiscible with the fluid at the first pressure and at the temperature conditions used. In some embodiments, the sample is collected with a needle inserted into the pressure chamber. Any aspect of an embodiment of the method of determining MMP can be incorporated into various embodiments of the method sampling one or more components of the oil composition.

Visual observations have shown that crude oil hydrocarbons are mobilized into the upper (mobile) phase of an injected fluid including but not limited to $CO_2$ and natural gas. Contrary to conventional wisdom that says the MMP must be exceeded before significant hydrocarbon mobilization occurs, high pressure view cells show clearly that significant amounts of oil hydrocarbons can be mobilized into the upper injected fluid phase at pressures substantially below MMP, and that increasing amounts of hydrocarbon continue to be mobilized as pressure is increased to, and then above the MMP. Similarly, large amounts of oil hydrocarbons can precipitate from the upper mobile phase back into the lower bulk oil phase as the pressure is dropped from above MMP to a lower value (but still above MMP). As the pressure of the injected fluid is further dropped below MMP, large amounts of oil can continue to be lost from the upper mobile phase. These results, combined with the common observation that $CO_2$ enhanced oil recovery (EOR) floods can produce lighter crudes than the original oil demonstrate a need to determine the mobilized hydrocarbon composition (including both the mass of oil mobilized and its molecular weight distribution) in samples collected at both pressures and temperatures representative of EOR reservoir conditions.

In various embodiments, the present invention provides an apparatus and method that allows a sample to be collected at any position in a high-pressure view cell, e.g., to collect a sample of hydrocarbons either in the upper mobile phase or lower bulk oil phase, or in any additional extract phases of mixed injected fluid and oil hydrocarbons that may form ion the view cell. Samples of hydrocarbon can be collected from any position in the high-pressure view cell without disturbing either the pressure or temperature of the device, thus ensuring that the collected hydrocarbons accurately represent the hydrocarbon composition under the EOR conditions being simulated in the high pressure cell. The samples can be collected in a manner that allows for hydrocarbon analysis by conventional gas chromatography techniques. The apparatus and method have been used successfully to collect samples of mobilized oil hydrocarbons at pressures below, at, and above MMP, and at various temperatures representing reservoir conditions ranging from conventional shallower (cooler) reservoirs to deep (hotter) unconventional reservoirs, and has shown that large changes in the both the quantity of hydrocarbon and the molecular weight distribution of mobilized hydrocarbons varies dramatically as pressure of the injected fluid is varied from below, to, and above MMP. The method can be useful in better understanding and designing EOR floods.

In some embodiments, the method includes characterizing at least one aspect of the sample. For example, the method can include performing mass spectrometry, nuclear magnetic resonance spectroscopy, or infrared spectrometry on the sample to elucidate various aspects of the structures properties or characteristics. The method can provide a simple way to characterize the components of an oil composition that are miscible or immiscible with the fluid at various temperatures and pressures, and can be used to determine which fluids and which pressures should be used in a subterranean treatment to recover desired components of the oil composition, such as by selecting a pressure and fluid composition which will substantially cause one or more desired components of the oil composition to be miscible in the fluid.

Various embodiments of the present invention provide an apparatus for sampling at least one component of an oil composition. The apparatus includes a pressure chamber configured to have oil composition therein. The pressure chamber is configured to have a fluid including at least one of a gas, a liquid, and a supercritical fluid placed therein at a first pressure sufficient to contact the oil composition. The pressure chamber is configured such that a sample of at least one of the fluid and the oil composition can be taken at the first pressure.

The pressure chamber can be any suitable size, such that it can include the oil composition, and the fluid. The oil composition sample can be any suitable size, and the fluid that enters the pressure chamber can be any suitable quantity. The apparatus, including the pressure chamber, can be scaled up or down without limitation. In some embodiments, the method can include cleaning the pressure chamber prior to placing the oil composition and the fluid therein. In some embodiments, the method can include evacuating other gases from the pressure chamber prior to placing the oil composition and the fluid therein. The evacuating can be performed in any suitable way. For example, prior to adding the oil composition to the pressure chamber, the fluid can be added to the pressure chamber and allowed to flow therethrough such that contaminating materials are flushed out, or a vacuum can be applied to the pressure chamber and the fluid can be allowed to flow in to relieve the vacuum (for one or more cycles). In various embodiments, the accuracy of the method can be improved by cleaning the pressure chamber and by removing atmospheric gases or other gases from the pressure chamber prior to adding the fluid and the oil composition thereto.

The method can include placing the fluid into the pressure chamber at a first pressure. The first pressure can be any suitable pressure in the pressure chamber, wherein the first pressure can be any suitable pressure, such as a pressure lower than, equal to, or greater than the MMP of the fluid and the oil composition. The first pressure can be similar to a downhole pressure, such as a pressure wherein the oil composition was obtained. The first pressure can be achieved by any suitable means. For example, the fluid can flow to the pressure chamber from a pressurized source, and a valve between the pressurized source and the pressure chamber can be opened to raise the pressure. In some embodiments, the pressure, temperature, or both, of the fluid and the oil composition is allowed to equilibrate. Any suitable degree of equilibration can be performed. The equilibration can include allowing the system to stabilize for about 0.1 second to about 4 hours, or about 0.1 second or less, or about 1 second, 5 seconds, 10 seconds, 20 seconds, 30 seconds, 45 seconds, 1 minutes, 2 minutes, 3 minutes, 4 minutes, 5 minutes, 10 minutes, 20 minutes, 30 minutes, 45 minutes, 60 minutes, 2 hours, 3 hours, or about 4 hours or more, wherein during the stabilization, the oil composition and the fluid can obtain at least one or a more even pressure and temperature, and the oil composition and fluid can partition such that none of the oil composition is stably miscible with the fluid or such that some proportion of the oil composition becomes stably miscible with the fluid.

Additional Embodiments

The following exemplary embodiments are provided, the numbering of which is not to be construed as designating levels of importance:

Embodiment 1 provides a method of sampling one or more components of an oil composition, the method comprising:

placing a fluid into a pressure chamber at a first pressure, the pressure chamber comprising an oil composition therein sufficient to contact the fluid, wherein the fluid comprises at least one of a gas, a liquid, and a supercritical fluid; and taking a sample of at least one of the fluid and the oil composition from the pressure chamber.

Embodiment 2 provides the method of Embodiment 1, further comprising characterizing at least one aspect of the sample.

Embodiment 3 provides the method of any one of Embodiments 1-2, further comprising equilibrating pressure within the pressure chamber prior take the sample.

Embodiment 4 provides the method of any one of Embodiments 1-3, wherein the first pressure is about equal to a downhole pressure of crude oil in a subterranean formation.

Embodiment 5 provides the method of any one of Embodiments 1-4, further comprising equilibrating temperature within the pressure chamber prior to taking the sample.

Embodiment 6 provides the method of any one of Embodiments 1-5, wherein a temperature within the pressure chamber is about equal to a downhole temperature of crude oil in a subterranean formation.

Embodiment 7 provides the method of any one of Embodiments 1-6, wherein the fluid comprises at least one of carbon dioxide, nitrogen, methane, ethane, propane, hydrogen sulfide, n-butane, iso-butane, natural gas, natural gas liquids, and produced gas.

Embodiment 8 provides the method of any one of Embodiments 1-7, wherein the oil composition comprises crude oil or a crude oil fraction.

Embodiment 9 provides the method of any one of Embodiments 1-8, wherein the oil composition comprises a live oil sample.

Embodiment 10 provides an apparatus for sampling at least one component of an oil composition, the apparatus comprising:

a pressure chamber configured to have oil composition therein, the pressure chamber configured to have a fluid comprising at least one of a gas, a liquid, and a supercritical fluid placed therein at a first pressure sufficient to contact the oil composition;

wherein the pressure chamber is configured such that a sample of at least one of the fluid and the oil composition can be taken at the first pressure.

Embodiment 11 provides the apparatus or method, of any one or any combination of Embodiments 1-10 optionally configured such that all elements or options recited are available to use or select from.

What is claimed is:

1. A method of enhanced oil recovery from a subterranean formation, the method comprising:

placing a fluid comprising at least one of a gas, a liquid, and a supercritical fluid (SCF) into a pressure chamber at a first pressure and temperature, the pressure chamber comprising an oil composition which is contacted with the fluid, the oil composition comprising a desired component;

varying at least one of pressure and temperature in the pressure chamber to provide one or more simulated reservoir conditions;

taking one or more samples of at least one of the fluid and the oil composition at the simulated reservoir conditions from the pressure chamber, comprising taking a sample of either an upper mobile phase or a lower bulk oil phase from the pressure chamber;

analyzing the samples to determine a pressure and temperature which causes a result of miscibility of the desired component with the fluid at a pressure other than the minimum miscibility pressure for the oil composition with the fluid, wherein the pressure chamber is configured to provide a sample of either the upper mobile phase or the lower bulk oil phase to a gas chromatography system for analysis of at least one of mass and molecular weight distribution of hydrocarbons in the sample corresponding to the simulated reservoir conditions; and using the result of the determination to inject another fluid having the same composition as the fluid placed in the pressure chamber into the subterranean formation to contact a crude oil at the determined pressure and temperature conditions in the subterranean formation to induce a separation of the desired component from the crude oil into the fluid.

2. The method of claim 1, further comprising analyzing the sample to determine the mass and molecular weight distribution of hydrocarbons in the fluid.

3. The method of claim 1, further comprising equilibrating pressure within the pressure chamber prior to taking the sample.

4. The method of claim 1, wherein the first pressure is about equal to a downhole pressure of crude oil in the subterranean formation.

5. The method of claim 1, further comprising equilibrating temperature within the pressure chamber prior to taking the sample.

6. The method of claim 1, wherein a temperature within the pressure chamber is about equal to a downhole temperature of crude oil in the subterranean formation.

7. The method of claim 1, wherein the fluid comprises at least one of carbon dioxide, nitrogen, methane, ethane, propane, hydrogen sulfide, n-butane, iso-butane, natural gas, natural gas liquids, and produced gas.

8. The method of claim 1, wherein the oil composition comprises crude oil or a crude oil fraction.

9. The method of claim 1, wherein the oil composition comprises a live oil sample.

10. An apparatus for use in the method of claim 1, the apparatus comprising:
a pressure chamber configured to have the oil composition therein, the pressure chamber configured to have a fluid comprising at least one of a gas, a liquid, and a supercritical fluid placed therein to contact the oil composition at a first pressure;
wherein the apparatus is configured to vary pressure and temperature in the pressure chamber to provide simulated reservoir conditions at which the oil composition becomes miscible with the fluid; and
wherein the pressure chamber is configured to provide a sample of at least one of the fluid and the oil composition, wherein the sample is either an upper mobile phase or a lower bulk oil phase from the pressure chamber, to a gas chromatography system for analysis of at least one of mass and molecular weight distribution of hydrocarbons in the sample, the sample having a mass and molecular weight distribution of hydrocarbons corresponding to the simulated reservoir conditions.

11. The method of claim 1, wherein the sample has a mass and molecular weight distribution of hydrocarbons corresponding to downhole conditions in the subterranean formation.

12. The method of claim 1, wherein the sample comprises a portion of the oil composition that is miscible with the fluid.

13. The method of claim 1, wherein the oil composition is obtained from the subterranean formation.

14. The method of claim 1, comprising varying the pressure to a pressure below minimum miscibility pressure of the oil composition so that the desired component of the oil composition becomes miscible with the fluid.

15. The method of claim 1, wherein the determined pressure is below minimum miscibility pressure of the oil composition.

16. The method of claim 1, comprising varying the pressure to a pressure above minimum miscibility pressure of the oil composition so that the desired component of the oil composition becomes miscible with the fluid.

17. The method of claim 1, wherein the determined pressure is above minimum miscibility pressure of the oil composition.

18. The method of claim 1, wherein the first pressure is below minimum miscibility pressure of the oil composition.

19. The method of claim 1, wherein the first pressure is above minimum miscibility pressure of the oil composition.

* * * * *